(12) United States Patent
Kudzma et al.

(10) Patent No.: US 8,729,313 B2
(45) Date of Patent: May 20, 2014

(54) PROCESS FOR THE MANUFACTURING OF SEVOFLURANE

(75) Inventors: Linas Kudzma, Annandale, NJ (US); Ronald Bell, Glen Gardner, NJ (US); Yongxian Zeng, Edison, NJ (US); Leonid A. Rozov, Fair Lawn, NJ (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 455 days.

(21) Appl. No.: 13/210,272

(22) Filed: Aug. 15, 2011

(65) Prior Publication Data
US 2013/0046117 A1    Feb. 21, 2013

(51) Int. Cl.
C07C 41/22   (2006.01)
C07C 41/38   (2006.01)
C07C 41/42   (2006.01)
C07C 43/12   (2006.01)

(52) U.S. Cl.
CPC ............. *C07C 41/22* (2013.01); *C07C 41/38* (2013.01); *C07C 41/42* (2013.01); *C07C 43/123* (2013.01)
USPC ........................................ 568/683; 568/682

(58) Field of Classification Search
CPC ................................ C07C 41/38; C07C 41/42
See application file for complete search history.

(56) References Cited

U.S. PATENT DOCUMENTS

| | | | |
|---|---|---|---|
| 3,476,860 A | 11/1969 | Croix et al. | |
| 3,527,814 A | 9/1970 | Croix et al. | |
| 4,250,334 A | 2/1981 | Coon et al. | |
| 4,469,898 A | 9/1984 | Coon et al. | |
| 5,233,098 A | 8/1993 | Nakazora et al. | |
| 5,679,576 A | 10/1997 | Kawai et al. | |
| 5,811,596 A | 9/1998 | Kawai et al. | |
| 5,886,239 A | 3/1999 | Kudzma et al. | |
| 5,969,193 A | 10/1999 | Terrell | |
| 5,990,359 A | 11/1999 | Ryan et al. | |
| 6,100,434 A | 8/2000 | Bieniarz et al. | |
| 6,469,219 B1 | 10/2002 | Khrimian et al. | |
| 6,987,204 B2 | 1/2006 | Rozov et al. | |
| 7,202,386 B2 | 4/2007 | Terrell | |
| 7,230,143 B2 | 6/2007 | Jones et al. | |
| 7,375,254 B2 | 5/2008 | Rozov et al. | |

FOREIGN PATENT DOCUMENTS

WO    WO-02/50003 A1    6/2002
WO    WO-02/50005 A1    6/2002

OTHER PUBLICATIONS

Kudzma et al., Diisopropylethylamine mono(hydrogen fluoride) for nucleophilic fluorination of sensitive substrates: synthesis of sevoflurane, J. Fluor. Chem., 111(1):11-16 (2001).
Bieniarz et al., "An efficient and environmentally friendly synthesis of the inhalation anesthetic sevoflurane", J. Fluorine Chem., 106:99-102 (2000).
International Search Report and Written Opinion from corresponding international application No. PCT/US2012/049558, mailing date Nov. 19, 2012.

*Primary Examiner* — Rosalynd Keys
(74) *Attorney, Agent, or Firm* — Marshall, Gerstein & Borun LLP

(57) ABSTRACT

The present invention provides a method for forming sevoflurane comprising (i) combining chlorosevo ether, a nucleophilic fluoride reagent, and a solvent comprising sevoflurane to form an initial reaction mixture and (ii) reacting the initial reaction mixture to form additional sevoflurane relative to the amount of sevoflurane present in the initial reaction mixture. The present disclosure is also directed to a method for forming sevoflurane, comprising: initiating a reaction between chlorosevo ether and a nucleophilic fluoride reagent in an initial reaction mixture further comprising a solvent comprising sevoflurane, thereby forming additional sevoflurane relative to the amount of sevoflurane present in the initial reaction mixture.

34 Claims, No Drawings

PROCESS FOR THE MANUFACTURING OF SEVOFLURANE

BACKGROUND

1. Field of the Disclosure

The disclosure relates generally to methods of preparing sevoflurane (1,1,1,3,3,3-hexafluoro-2-(fluoromethoxy)propane). More particularly, the disclosure is directed to the synthesis of sevoflurane from the reaction of chlorosevo ether (1,1,1,3,3,3-hexafluoro-2-(chloromethoxy)propane) and a nucleophilic fluoride reagent, using the desired end-product of sevoflurane as a solvent.

2. Brief Description of Related Technology

Sevoflurane is a halogenated, volatile anesthetic typically administered by inhalation to induce and/or maintain general anesthesia. U.S. Pat. No. 5,886,239 describes a process for synthesizing sevoflurane involving the fluorination of chlorosevo ether with an amine hydrofluoride salt. The '239 patent discloses that a molar excess of the precursor chlorosevo ether can be included in the reaction to act as a solvent (column 3, lines 38-42). In Example 1, a 0.5 molar excess of chlorosevo ether (corresponding to an initial reaction mixture containing 1.5 molar equivalents of chlorosevo ether relative to 1.0 molar equivalent of HF) is used in the synthesis to yield an organic layer containing 63.6% sevoflurane and 35.4% chlorosevo ether. While a 95% conversion yield of sevoflurane (based on the starting material consumed) is achieved in the exemplified synthesis, it is necessary for the remaining, unreacted, excess chlorosevo ether, which is a valuable precursor reagent, to be recovered and purified so that it may be reused in subsequent reactions.

Additionally, the synthesis of sevoflurane from excess chlorosevo ether and a nucleophilic fluoride reagent has been found to yield other impurities such as hexafluoroisopropanol (HFIP), sevomethyl ether (SME), and high boiling oligomeric products derived from chlorosevo ether.

Since sevoflurane should be substantially free from impurities for use in pharmaceutical applications, improved methods for producing sevoflurane are desirable, particularly methods that provide sevoflurane at a higher purity and/or simplify the processing of the reaction product while increasing or maintaining the conversion yields achieved in the '239 patent.

SUMMARY

In one embodiment, the invention provides a method for forming sevoflurane comprising (i) combining chlorosevo ether, a nucleophilic fluoride reagent, and a solvent comprising sevoflurane to form an initial reaction mixture, and (ii) reacting the initial reaction mixture to form additional sevoflurane relative to the amount of sevoflurane present in the initial reaction mixture.

In another embodiment, the invention provides a method for forming sevoflurane comprising initiating a reaction between chlorosevo ether and a nucleophilic fluoride reagent in an initial reaction mixture further comprising a solvent comprising sevoflurane, thereby forming additional sevoflurane relative to the amount of sevoflurane present in the initial reaction mixture.

DETAILED DESCRIPTION

The present invention is generally directed to methods for forming sevoflurane from the reaction of chlorosevo ether with a nucleophilic fluoride reagent characterized by the use of the desired-end product of sevoflurane as a solvent (i.e., sevoflurane is present in the initial reaction mixture ab initio). Surprisingly and unexpectedly, the use of the desired end-product sevoflurane as a solvent in the methods according to the invention facilitates the production of additional sevoflurane in high yield and purity.

As mentioned above, the '239 patent discloses the use of excess chlorosevo ether as a solvent. When chlorosevo ether is fluorinated to produce sevoflurane using a nucleophilic fluoride reagent such as an amine hydro fluoride salt, the amine hydro fluoride salt is converted to an amine hydrochloride salt. In the absence of excess chlorosevo ether, the inventors found that the amine hydrochloride salt produced during the reaction crystallizes upon cooling to ambient temperature, thereby hindering emptying of the reaction vessel and washing of the crude product.

The inventors also found, however, that there are disadvantages associated with the use of excess chlorosevo ether as a solvent in the synthesis of sevoflurane as disclosed in the '239 patent. For example, the inventors observed that chlorosevo ether can degrade during the reaction between chlorosevo ether and the nucleophilic fluoride reagent, producing impurities such as hexafluoroisopropanol, formaldehyde, and hydrogen chloride (HCl). The aforementioned impurities can remain in the crude product, or can recombine to produce undesirable side products such as sevomethyl ether and high boiling oligomeric products.

As mentioned previously, chlorosevo ether is a valuable precursor reagent that for economy and efficiency reasons must be recovered after the reaction is complete so that it can be recycled and reused in subsequent reactions. However, the inventors have discovered that chlorosevo ether can degrade during the recovery process as well, such that a substantial portion of the valuable chlorosevo ether is irretrievably lost. Furthermore, the HCl produced from the decomposition of chlorosevo ether during its recovery is highly corrosive to distillation equipment.

In contrast to both the '239 patent, which uses excess chlorosevo ether as a solvent, and other methods that utilize compounds such as water as solvents in methods for forming sevoflurane, the methods according to the invention are counterintuitive in that the desired reaction end-product of sevoflurane is used as a solvent such that it is present ab initio in the initial reaction mixture with the initially present amounts of the reactants of chlorosevo ether and nucleophilic fluoride reagent. By substituting the desired end-product of sevoflurane for the excess amount of chlorosevo ether which functions as a solvent in the synthetic method according to the '239 patent, the yields and purity of the sevoflurane produced in accordance with the methods of the invention are improved. More specifically, the use of the desired end-product of sevoflurane as a solvent in the methods according to the invention unexpectedly and surprisingly results in the generation of fewer by-products, thereby providing sevoflurane at higher purity and simplifying the purification process. Further, the problems associated with recovering and purifying any remaining, unreacted, excess chlorosevo ether from the reaction product are eliminated as substantially all of the chlorosevo ether starting material is advantageously converted to sevoflurane in the methods according to the invention.

In one embodiment, the invention provides a method for forming sevoflurane comprising (i) combining chlorosevo ether, a nucleophilic fluoride reagent, and a solvent comprising sevoflurane to form an initial reaction mixture and (ii) reacting the initial reaction mixture to form additional sevoflurane relative to the amount of sevoflurane present in the initial reaction mixture. The additional sevoflurane produced from this reaction is distinct from the sevoflurane present (as a solvent) in the initial reaction mixture and is generated from the fluorination of chlorosevo ether.

In a further embodiment, the present disclosure is also directed to a method for forming sevoflurane comprising initiating a reaction between chlorosevo ether and a nucleophilic fluoride reagent in an initial reaction mixture further comprising a solvent comprising sevoflurane, thereby forming additional sevoflurane relative to the amount of sevoflurane present in the initial reaction mixture. As in the first embodiment, the additional sevoflurane produced from this reaction is distinct from the sevoflurane present in the initial reaction mixture and is generated from the fluorination of chlorosevo ether.

As used herein, the term "nucleophilic fluoride reagent" refers to a reagent capable of causing nucleophilic substitution by fluoride for another anion.

As used herein, the term "solvent" refers to a liquid component in the initial reaction mixture that dissolves and/or is miscible with a solid, liquid, and/or gaseous solute, to form a solution. Thus, the term solvent does not encompass solutes such as salts or stoichiometric amounts of reactants that are reacted/consumed during the reaction according to the invention.

The solvent comprising sevoflurane present in the initial reaction mixture can be greater than 70 wt. % sevoflurane, greater than 80 wt. % sevoflurane, greater than 90 wt. % sevoflurane, greater than 95 wt. % sevoflurane, greater than 97 wt. % sevoflurane, and/or greater than 99 wt. % sevoflurane. Further, the solvent comprising sevoflurane can be substantially free of water. In the context of this invention, "substantially free of water" means that the solvent comprising sevoflurane contains less than about 3 wt. % of water, based on the total weight of the solvent in the initial reaction mixture. More preferably, the solvent comprising sevoflurane contains less than about 2 wt. %, less than 1 wt. %, and/or less than about 0.5 wt. % of water, based on the total weight of the solvent in the initial reaction mixture.

Typically, the initial reaction mixture contains sevoflurane and chlorosevo ether in a molar ratio of about 0.2:1 to about 1:1, for example, about 0.3:1 to about 1:1, about 0.4:1 to about 1:1, about 0.5:1 to about 1:1, about 0.6:1 to about 1:1, about 0.7:1 to about 1:1, about 0.8:1 to about 1:1, and/or about 0.9:1 to about 1:1. Most preferably, the sevoflurane is present in the initial reaction mixture in an amount sufficient to dissolve any salts and/or complexes of salts present in the reaction mixture (whether the salts are initially present and/or generated during the reaction). A molar ratio of sevoflurane to chlorosevo ether of about 0.2:1 to about 1:1, more preferably 0.3:1 to about 0.7:1, most preferably about 0.5:1, is typically sufficient for this purpose. As sevoflurane is preferably initially present in an amount sufficient to dissolve the salts present in the reaction mixture, no additional solvents are necessary to efficiently convert chlorosevo ether to sevoflurane in accordance with the methods of the invention, but optionally other solvents may also be present.

Similarly, the initial mixture generally contains sevoflurane, chlorosevo ether, and the nucleophilic fluoride reagent in a molar ratio of about 0.2:1:1 to about 1:1:1.5, for example, about 0.3:1:1 to about 1:1:1.5, about 0.4:1:1 to about 1:1:1.5, about 0.5:1:1 to about 1:1:1.5, about 0.6:1:1 to about 1:1:1.5, about 0.7:1:1 to about 1:1:1.5, about 0.8:1:1 to about 1:1:1.5, and/or about 0.9:1:1 to about 1:1:1.5. Preferably, excess nucleophilic fluoride reagent is included in the initial reaction mixture in order to facilitate the substantially complete conversion of the valuable cholorosevo ether precursor material.

A molar ratio of chlorosevo ether to nucleophilic fluoride reagent of about 1:1 to about 1:1.5, more preferably 1:1.05 to about 1:1.35, most preferably about 1:1.25, is typically sufficient for this purpose. Thus, the initial mixture can contain sevoflurane, chlorosevo ether, and the nucleophilic fluoride reagent in a molar ratio of about 0.2:1:1.05 to about 1:1:1.35 (in addition to the other ratios mentioned above).

In the methods according to the invention, the additional sevoflurane is typically formed in an amount of about 0.5 mole to about 1.0 mole (formed) sevoflurane per mole of the chlorosevo ether reactant, for example, about 0.6 mole sevoflurane per mole chlorosevo ether, about 0.7 mole sevoflurane per mole chlorosevo ether reactant, about 0.8 mole sevoflurane per mole chlorosevo ether reactant, about 0.9 mole sevoflurane per mole chlorosevo ether reactant, and most preferably greater than 0.95 mole sevoflurane per mole chlorosevo ether reactant. The additional sevoflurane formed from this reaction is distinct from the sevoflurane used as a solvent in the initial reaction mixture and is generated from the fluorination of chlorosevo ether. Therefore, the maximum amount of additional sevoflurane produced during this reaction is equivalent to the molar amount of chlorosevo ether used in the initial reaction mixture assuming 100% conversion.

Suitable nucleophilic fluoride reagents include, but are not limited to, hydrogen fluoride, fluoride salts (e.g., KF, NaF, tetraalkyl ammonium fluorides such as tetrabutyl ammonium fluoride), crown ether complexes of alkali fluoride salts, hydrofluoride salts (e.g., amine hydrofluoride salts), hydrogen fluoride complexes (e.g., amine tris-hydrogen fluoride complexes), and combinations thereof. Nucleophilic fluoride reagents comprising a combination of a tertiary amine and hydrogen fluoride such as amine hydrofluoride salts and amine tris-hydrogen fluoride complexes are typically soluble in sevoflurane (and thus also in solvents comprising sevoflurane) and are therefore preferred, particularly where the tertiary amine is a sterically hindered amine as described below.

Suitable amines for forming amine hydro fluoride salts and amine tris-hydrogen fluoride complexes include but are not limited to tertiary amines. Exemplary tertiary amines include but are not limited to trialkylamines such as trimethylamine, triethylamine, diethylmethylamine, dimethylethylamine, tripropylamine, triisopropylamine, n-tributylamine, tripentylamine, trihexylamine, triheptylamine, trioctylamine, and cyclic tertiary amines such as N-methylpyrrolidine, and 1,4-diazabicyclo[2.2.2]octane, and mixtures of the foregoing. Sterically hindered tertiary amines as disclosed in U.S. Pat. No. 5,886,239, the disclosure of which is hereby incorporated by reference, are preferred. Preferred sterically hindered tertiary amines are selected from those represented by the following formula:

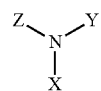

wherein X, Y, and Z are independently selected from lower alkyl groups, branched lower alkyl groups, and cyclo-lower alkyl groups, and wherein at least one of X, Y, and Z is a branched lower alkyl group or cyclo-lower alkyl group. The term "lower alkyl" as used herein refers to saturated alkyl groups containing 1 to 6 carbons which are straight-chain groups unless specifically stated otherwise. Examples of representative branched- and cyclo-lower alkyl groups present in compounds of the above formula include isopropyl, tert-butyl, neopentyl, cyclohexyl, and the like. In a preferred embodiment of the invention, the sterically hindered tertiary amine is diisopropylethylamine.

In one embodiment, the nucleophilic fluoride reagent is formed by combining an amine and hydrogen fluoride in the reaction mixture, so as to form an amine hydrofluoride salt in situ. In another embodiment, the nucleophilic fluoride reagent is prepared in advance, for example, by reacting either anhydrous HF or a concentrated aqueous solution of HF with an amine such as diisopropylethylamine so as to form an amine hydrofluoride salt, and then added to the reaction mixture. In both embodiments, the amine and hydrogen fluoride are generally combined in a molar ratio of about 1:1 to about 1.2:1 such that there is a slight excess of amine present. For example, the molar ratio of amine to hydrogen fluoride can be about 1.01:1 to about 1.1:1 including but not limited to about 1.05:1.00.

Alternatively, a previously prepared stable amine tris-hydrogen fluoride complex formed by combining three molar equivalents of HF and 1 molar equivalent of tertiary amine (preferably, a sterically hindered tertiary amine as described above) can be added to the initial reaction mixture and subsequently treated with two molar equivalents of tertiary amine (preferably, a sterically hindered tertiary amine as described above) to form three molar equivalents of the amine hydrofluoride salt in situ.

The conversion of chlorosevo ether to sevoflurane in accordance with the present invention can be conducted at elevated temperatures, for example, a temperature greater than 30° C. The reaction can be suitably conducted at a temperature in the range of about 30° C. to about 200° C., about 35° C. to about 180° C., about 40° C. to about 150° C., and/or about 50° C. to about 120° C., at atmospheric (using an open reactor) or elevated pressure (using a closed reactor). When an open reactor is used, the reaction is typically conducted at the reflux temperature. For example, the initial reaction mixture of chlorosevo ether, sevoflurane, and the nucleophilic fluoride is generally heated under reflux conditions for about 1 to about 36 hours, for example, about 10 to 30 hours. When a closed reactor is used, the reaction is generally conducted at temperatures greater than 50° C. and at elevated pressure. For example, the reaction can be conducted in a sealed pressure vessel at a pressure greater than 5 psi, such as in the range of about 5 psi to about 120 psi, about 15 psi to about 100 psi, and/or about 20 psi to about 50 psi. In both closed and open reactors, the reaction is typically considered to be complete when greater than 90% and more preferably when greater than 95% of the chlorosevo ether has been converted to sevoflurane, as can be easily determined by one having ordinary skill in the art.

While the present invention eliminates the need to remove and recover excess chlorosevo ether from the obtained sevoflurane product, and reduces the amounts of hexafluoroisopropanol, sevomethyl ether, and high boiling oligomeric products generated during the reaction and thus present in the crude reaction product, it is generally desirable to remove any impurities remaining in the reaction medium after the reaction according to the invention is complete. In one embodiment, the sevoflurane can be isolated from the crude reaction product mixture (i.e., after the initial reaction mixture has been reacted) by washing the mixture with water, separating the organic and aqueous layers, and then washing the organic layer with an aqueous acidic solution such as 5% aqueous hydrochloric acid to yield crude sevoflurane. Alternatively or in conjunction with the aforementioned washing steps, the crude sevoflurane can be isolated and purified by steam distillation or fractional distillation.

The disclosure may be better understood by reference to the following examples which are not intended to be limiting, but rather only set forth exemplary embodiments in accordance with the disclosure.

EXAMPLES

Example 1

Preparation of Sevoflurane in an Open Reactor

Chlorosevo ether (272.0 g, 1.256 mol), sevoflurane (125.6 g, 0.628 mol) and diisopropylethylamine (203.5 g, 1.575 mol) were combined in a TEFLON® reactor to form a mixture. The mixture was cooled to 10-12° C., and anhydrous, liquid hydrogen fluoride (30.0 g, 1.5 mol) was then added over a period of about 20 min. The total content of amine present was in 5% molar excess to that of hydrogen fluoride. The resulting reaction mixture was heated at reflux for 20 hrs and then cooled to room temperature. No salts crystallized upon cooling to ambient temperature. The product was isolated by washing the reaction mixture once with water (50% volume) and then the organic and aqueous layers were separated. The organic layer was then washed with an aqueous 5% hydrochloric acid solution, yielding 359.0 g of light yellow crude sevoflurane.

Ten additional runs using substantially the same amounts of chlorosevo ether, sevoflurane, diisopropylethylamine, and hydrogen fluoride were carried out as described above to produce 3430 grams of crude sevoflurane which were charged to a 3 L three-neck PYREX® round-bottom flask. The sevoflurane was distilled in a vacuum jacketed 6 ft×1 inch column topped with a solenoid controlled liquid dividing splitter head equipped with a reflux timer, thermocouple, and reflux condenser and receiver. The distillation was equilibrated at reflux overnight and then distilled. The fractions were analyzed by gas chromatography on a CARBOBLACK™ B packed column loaded with 5% RT-1000 (Restek Corporation, Bellefonte, Pa.). Analysis of the collected fractions is provided in Table 1.

TABLE 1

Analysis of Fractions from Flash Distillation.
Results are Normalized Weight Percent.

| Sample | Sevoflurane | Cl-sevo | SME | HFIP |
|---|---|---|---|---|
| Fraction 1, 69 g | 99.10 | 0.00* | 0.01 | 0.63 |
| Fraction 2, 68 g | 99.07 | 0.00* | 0.00* | 0.85 |
| Fraction 3, 70 g | 99.44 | 0.00* | 0.00* | 0.52 |
| Fraction 4, 69 g | 99.22 | 0.00* | 0.00* | 0.72 |
| Fraction 5, 343 g | 99.95 | 0.00* | ND | 0.05 |
| Fraction 6, 349 g | 99.98 | 0.00* | ND | 0.01 |
| Fraction 7, 339 g | 99.99 | 0.00* | ND | 0.01 |
| Fraction 8, 363 g | 99.99 | 0.00* | ND | 0.01 |
| Fraction 9, 355 g | 99.98 | 0.00* | ND | 0.01 |
| Fraction 10, 341 g | 99.99 | 0.00* | ND | 0.00 |
| Fraction 11, 68 g | 99.99 | 0.00* | ND | 0.01 |
| Fraction 12, 69 g | 99.99 | 0.00* | ND | 0.00 |
| Fraction 13, 76 g | 99.99 | 0.00* | ND | 0.00 |
| Fraction 14, 75 g | 99.99 | 0.00* | ND | 0.01 |
| Pot Residue, 685 g | 96.65 | 1.59 | 0.03 | 0.03 |

*Less than 10 ppm
ND = Not detected
Chlorosevo ether ("Cl-sevo"), sevomethyl ether ("SME"), hexafluoroisopropanol ("HFIP")

Example 2

Preparation of Sevoflurane in a Closed Reactor

Chlorosevo ether (190.3 g, 0.879 mol), sevoflurane (87.9 g, 0.439 mol) and diisopropylethylamine (142.5 g, 1.103 mol) were combined in a MONEL® Parr pressure reactor (Parr Instrument Company, IL). The solution was cooled to 4-5° C., and anhydrous, liquid hydrogen fluoride (21.0 g, 1.05 mol) was added to this mixture over 20 min. The total content of amine present was in 5% molar excess to that of hydrogen fluoride. The Parr reactor was then sealed and the resulting reaction mixture was stirred and heated at 100° C. for 5.5 hrs. The maximum pressure developed was about 20-30 psi. After cooling the reaction overnight to room temperature, the reactor was opened and the product was isolated by washing the reaction mixture once with water (50% volume) and then the organic and aqueous layers were separated. No salts crystallized upon cooling to ambient temperature. The organic layer was then washed with an aqueous 5% hydrochloric acid solution, yielding 248.0 g of light yellow crude sevoflurane.

Example 3

Comparative Example 1.5 molar equivalents of chlorosevo ether were reacted with 1.0 molar equivalents of anhydrous HF and 1.05 molar equivalents of diisopropylethylamine in accordance with the synthetic method using excess chlorosevo ether as the solvent according to the '239 patent. Conversion yields of about 95% were typically observed, but the produced sevoflurane must be separated from the excess chlorosevo ether used as a solvent and then the excess chlorosevo ether must be recovered and purified so that it may be reused in subsequent reactions.

Example 4

Analysis of Sevoflurane

The crude sevoflurane obtained from both the open and closed reactor fluorinations of Examples 1 and 2 was analyzed by gas chromatography on a CARBOBLACK™ B packed column loaded with 5% RT-1000 (Restek Corporation, Bellefonte, Pa.), and compared to the crude fluorination product obtained from the synthetic method using excess chlorosevo ether as the solvent according to the '239 patent (as described in Comparative Example 3). The analytical data is summarized in Table 2 and shows that the improved methods of forming sevoflurane according to the invention produce markedly purer product with significantly less hexafluoroisopropanol (HFIP) and higher boiling oligomeric products and somewhat less sevomethyl ether (SME).

TABLE 2

Analysis of Comparative and Improved Fluorination Crude Products.

| Sample Description | Crude fluorination product from Comparative Example 3 | Crude fluorination product from Example 1 | Crude fluorination product from Example 2 |
|---|---|---|---|
| Sevoflurane (%) | 67.051 | 99.339 | 99.206 |
| Cl-Sevo (%) | 30.683 | 0.2003 | 0.1186 |
| HFIP (%) | 1.960 | 0.2000 | 0.3753 |
| SME (%) | 0.007 | 0.0054 | 0.0057 |
| Dichloromethane (%) | 0.003 | ND | ND |
| HFIP Formate (%) | ND | 0.0004 | 0.0005 |

TABLE 2-continued

Analysis of Comparative and Improved Fluorination Crude Products.

| Sample Description | Crude fluorination product from Comparative Example 3 | Crude fluorination product from Example 1 | Crude fluorination product from Example 2 |
|---|---|---|---|
| Total Others (%) (including higher boiling oligomeric products) | 2.266 | 0.4603 | 0.6753 |

ND = Not detected.

Example 5

Analysis of Recovered DIPEA

The amines recovered from Example 1, which uses sevoflurane as a solvent in accordance with the methods of the invention, were analyzed by gas chromatography, and compared with the amines recovered from the synthetic method using excess chlorosevo ether as the solvent according to the '239 patent (as described in Comparative Example 3). The results are summarized in Table 3 and show that the use of sevoflurane as a solvent reduces the amount of diisopropylmethylamine (DIPMA) and diisopropylamine (DIPA) side products, thereby significantly improving the quality of the diisopropylethylamine (DIPEA) recycled from the fluorination reaction.

TABLE 3

Analysis of DIPEA Recovered from Comparative and Improved Fluorination Reactions.

| Sample Description | Amines recovered from Comparative Example 3 | Amines recovered from Example 1 |
|---|---|---|
| Diisopropylethylamine (DIPEA) (%) | 99.4531 | 99.6848 |
| Diisopropylamine (DIPA) (%) | 0.1071 | 0.0668 |
| Diisopropylmethylamine (DIPMA) (%) | 0.0994 | 0.0194 |

Example 6

Preparation of Sevoflurane in a Closed Reactor

Chlorosevo ether (1 molar equivalent), sevoflurane (0.7 molar equivalents) and triethylamine (1.25 molar equivalents) are combined in a MONEL® Parr pressure reactor (Parr Instrument Company, IL). The solution is cooled to 4-5° C., and anhydrous hydrogen fluoride (1.20 molar equivalents) is added to this mixture over 20 min. The Parr reactor is then sealed and the resulting reaction mixture is stirred and heated at 100° C. for 10.5 hrs. After cooling the reaction to room temperature, the reactor is opened and the product is isolated by washing the reaction mixture once with water (50% volume) and then the organic and aqueous layers were separated. The organic layer is then distilled.

Example 7

Preparation of Sevoflurane in an Open Reactor

Chlorosevo ether (1 molar equivalent), sevoflurane (0.70 molar equivalents), NaF (1.20 molar equivalents), and sufficient diglyme to dissolve the NaF are combined in a TEFLON® reactor to form a mixture. The resulting reaction mixture is heated at reflux and then cooled to room temperature. The product is isolated by washing the reaction mixture once with water (50% volume) and then the organic and aqueous layers are separated. The organic layer is then distilled.

Example 8

Preparation of Sevoflurane in an Open Reactor

Chlorosevo ether (1 molar equivalent), sevoflurane (0.5 molar equivalents), KF (1.20 molar equivalents), and tetrabutyl ammonium chloride (0.20 molar equivalents) are combined in a TEFLON® reactor to form a mixture. The resulting reaction mixture is heated at reflux and then cooled to room temperature. The product is isolated by washing the reaction mixture once with water (50% volume) and then the organic and aqueous layers are separated. The organic layer is then distilled.

What is claimed is:

1. A method for forming sevoflurane, comprising:
   (i) combining chlorosevo ether, a nucleophilic fluoride reagent, and a solvent comprising sevoflurane to form an initial reaction mixture; and,
   (ii) reacting the initial reaction mixture to form additional sevoflurane relative to the amount of sevoflurane present in the initial reaction mixture.
2. The method according to claim 1, wherein the nucleophilic fluoride reagent comprises a combination of an amine and hydrogen fluoride.
3. The method according to claim 2, wherein the amine is a tertiary amine.
4. The method according to claim 2, wherein the amine is a trialkylamine.
5. The method according to claim 2, wherein the amine is selected from the group consisting of trimethylamine, triethylamine, diethylmethylamine, dimethylethylamine, tripropylamine, triisopropylamine, n-tributylamine, tripentylamine, trihexylamine, triheptylamine, trioctylamine, N-methylpyrrolidine, 1,4-diazabicyclo[2.2.2]octane, and mixtures thereof.
6. The method according to claim 2, wherein the amine is diisopropylethylamine.
7. The method according to claim 2, wherein the amine is a cyclic amine.
8. The method according to claim 2, wherein the amine is a sterically hindered tertiary amines having the following formula:

wherein X, Y, and Z are independently selected from lower alkyl groups, branched lower alkyl groups, and cyclo-lower alkyl groups, and at least one of X, Y, and Z is a branched lower alkyl group or cyclo-lower alkyl group.
9. The method according to claim 1, wherein the solvent comprising sevoflurane is substantially free of water.
10. The method according to claim 1, wherein the solvent comprising sevoflurane comprises greater than 70 wt. % sevoflurane.
11. The method according to claim 1, wherein the molar ratio of the sevoflurane to the chlorosevo ether in the initial reaction mixture is about 0.2:1 to about 1:1.
12. The method according to claim 1, wherein the initial reaction mixture is reacted by heating to a temperature greater than 30° C.
13. The method according to claim 1, wherein the initial reaction mixture is reacted under reflux conditions.
14. The method according to claim 1, wherein the initial reaction mixture is reacted under a pressure greater than 5 psi.
15. The method according to claim 1, further comprising isolating the sevoflurane after reacting the initial reaction mixture.
16. The method according to claim 1, further comprising purifying the sevoflurane after reacting the initial reaction mixture.
17. The method according to claim 16, wherein purifying comprises fractional distillation.
18. A method for forming sevoflurane, comprising:
    initiating a reaction between chlorosevo ether and a nucleophilic fluoride reagent in an initial reaction mixture further comprising a solvent comprising sevoflurane, thereby forming additional sevoflurane relative to the amount of sevoflurane present in the initial reaction mixture.
19. The method according to claim 18, wherein the nucleophilic fluoride reagent comprises a combination of an amine and hydrogen fluoride.
20. The method according to claim 19, wherein the amine is a tertiary amine.
21. The method according to claim 19, wherein the amine is a trialkylamine.
22. The method according to claim 19, wherein the amine is selected from the group consisting of trimethylamine, triethylamine, diethylmethylamine, dimethylethylamine, tripropylamine, triisopropylamine, n-tributylamine, tripentylamine, trihexylamine, triheptylamine, trioctylamine, N-methylpyrrolidine, 1,4-diazabicyclo[2.2.2]octane, and mixtures thereof.
23. The method according to claim 19, wherein the amine is diisopropylethylamine.
24. The method according to claim 19, wherein the amine is a cyclic amine.
25. The method according to claim 19, wherein the amine is a sterically hindered tertiary amines having the following formula:

wherein X, Y, and Z are independently selected from lower alkyl groups, branched lower alkyl groups, and cyclo-lower alkyl groups, and at least one of X, Y, and Z is a branched lower alkyl group or cyclo-lower alkyl group.
26. The method according to claim 18, wherein the solvent comprising sevoflurane is substantially free of water.
27. The method according to claim 18, wherein the solvent comprising sevoflurane comprises greater than 70 wt. % sevoflurane.
28. The method according to claim 18, wherein the molar ratio of the sevoflurane to the chlorosevo ether in the initial reaction mixture is about 0.2:1 to about 1:1.

29. The method according to claim 18, wherein the initial reaction mixture is reacted by heating the initial reaction mixture to a temperature greater than 30° C.

30. The method according to claim 18, wherein the initial reaction mixture is reacted under reflux conditions.

31. The method according to claim 18, wherein the initial reaction mixture is reacted under a pressure greater than 5 psi.

32. The method according to claim 18, further comprising isolating the sevoflurane after reacting the initial reaction mixture.

33. The method according to claim 18, further comprising purifying the sevoflurane after reacting the initial reaction mixture.

34. The method according to claim 33, wherein purifying comprises fractional distillation.

* * * * *